United States Patent [19]
Heffelfinger et al.

[11] Patent Number: 5,784,152
[45] Date of Patent: Jul. 21, 1998

[54] TUNABLE EXCITATION AND/OR TUNABLE DETECTION MICROPLATE READER

[75] Inventors: David M. Heffelfinger, San Pablo; Franklin R. Witney, Novato; Chris Cunanan, Bay Point, all of Calif.

[73] Assignee: Bio-Rad Laboratories, Hercules, Calif.

[21] Appl. No.: 729,111

[22] Filed: Oct. 11, 1996

Related U.S. Application Data

[63] Continuation-in-part of Ser. No. 405,468, Mar. 16, 1995, Pat. No. 5,591,981.

[51] Int. Cl.$^6$ .................... G01N 21/27; G01N 21/64
[52] U.S. Cl. .................... 356/73; 356/318; 356/417; 356/436; 356/344; 250/458.1
[58] Field of Search .................... 356/317, 318, 356/417, 73, 436, 440, 344; 250/458.1, 459.1, 461.1, 461.2

[56] References Cited

U.S. PATENT DOCUMENTS

| | | | |
|---|---|---|---|
| 4,319,271 | 3/1982 | Hurni et al. | |
| 4,498,780 | 2/1985 | Banno et al. | 356/440 |
| 4,626,684 | 12/1986 | Landa | 356/318 |
| 4,786,170 | 11/1988 | Groebler | |
| 4,877,966 | 10/1989 | Tomei et al. | |
| 4,935,875 | 6/1990 | Shah et al. | |
| 4,968,148 | 11/1990 | Chow et al. | 356/436 |
| 5,039,219 | 8/1991 | James et al. | |
| 5,062,942 | 11/1991 | Kambara | |
| 5,127,730 | 7/1992 | Brelje et al. | |
| 5,138,170 | 8/1992 | Nogouchi | |
| 5,213,673 | 5/1993 | Fujimiya | |
| 5,290,419 | 3/1994 | Kambara | |
| 5,303,026 | 4/1994 | Strobl | 356/318 |
| 5,307,144 | 4/1994 | Hiroshi et al. | 356/440 |
| 5,377,003 | 12/1994 | Lewis et al. | |
| 5,381,016 | 1/1995 | Moriya | |
| 5,422,719 | 6/1995 | Goldstein | |
| 5,436,718 | 7/1995 | Fernandes et al. | 356/318 |

FOREIGN PATENT DOCUMENTS

| | | |
|---|---|---|
| 68266 | 10/1991 | Austria |
| 2922788 | 12/1979 | Germany |
| 61-281945 | 12/1986 | Japan |
| WO/9010219 | 9/1990 | WIPO |

OTHER PUBLICATIONS

Cothren, R.M; "Gastronomical Tissue Diagnosis by Laser-Induced Fluorescence Spectroscopy Endoscopy," *Gastrointestinal Endoscopy*, vol. 36, No. 2 (Mar./Apr. 1990), pp. 105–111.

Anderson, P.S.; "Autofluorescence of Various Tissues and Human Skin Tumor Samples," *Lasers in Medical Science*, vol. 12, No. 1, (Jan.–Mar. 1987), pp. 41–49.

Ried, T.; "Simultaneous Visualization of Seven Different DNA Probes by in situ Hybridization Using Combinatorial Fluorescence and Digital Imaging Microscopy" *Proceedings of the National Academy of Science of the United States of America*, vol. 89, No. 4 (Feb. 15, 1992), pp. 1388–1392.

(List continued on next page.)

*Primary Examiner*—F. L. Evans
*Attorney, Agent, or Firm*—David G. Beck; Townsend and Townsend and Crew

[57] ABSTRACT

A method and apparatus of analyzing samples contained in a microplate is provided. The instrument is capable of measuring fluorescence, luminescence, and/or absorption within multiple locations within a sample well. The instrument is tunable over the excitation and/or detection wavelengths. Neutral density filters are used to extend the sensitivity range of the absorption measuring aspect of the instrument. Due to the wavelength tuning capabilities of the instrument, the spectral dependence of the measured fluorescence, luminescence, and absorption of the materials in question can be analyzed. The combination of a data processor and a look-up table improve the ease of operation of the instrument. Several different formats are available for the output data including creation of a bit map of the sample.

61 Claims, 6 Drawing Sheets

OTHER PUBLICATIONS

Product Literature: *Holographic Notch and Supernotch® Filters*, Kaiser Optical Systems, Inc. (1992).

David M. Rust, "Étalon Filters," *Optical Engineering*, vol. 33, No. 10, (Oct. 1994), pp. 3342–3348.

Marc Solioz, "Video Imaging of Ethidium Bromide–Stained DNA Gels with Surface UV Illumination," *Biotechniques*, vol. 16, No. 6 (1994), pp. 1130–1133.

Product Literature: *SD100 & SD200 Spectral Bio–Imaging Systems*, Spectral Diagnostics,Inc. (Nov. 9, 1994).

Aaron T. Thompson, et al., "Wavelength–Resolved Fluorescence Detection in Capillary Electrophoresis," *Analytical Chemistry*, vol. 67, No. 1 (Jan. 1, 1995), pp. 139–144.

Product Literature: *FMBIO 100 Fluorescent Imaging Device*, Hitachi Software (1993).

Product Literature: *Model 373A DNA Sequencing System*, Applied Biosystems.

Leroy E. Hood et al., "Automated DNA Sequencing and Analysis of the Human Genome," *Genomics 1*, (1987), pp. 201–212.

K.B. Bechtol et al., "Using Dyes and Filters in a Fluorescent Imaging System," American Biotechnology Laboratory (Dec. 1994), pp. 8–10.

Product Literature: *Digital Imaging Spectroscopy*, Kairos, Inc.

Christopher L. Stevenson et al., "Synchronous Luminescence: A New Detection Technique for Multiple Fluorescent Probes Used for DNA Sequencing," *Biotechniques*, vol. 16, No. 6, pp. 104–1106.

Product Literature: *Tunable Filters*, Cambridge Research Instrumentation, Inc.

Product Literature: *Biolumin Micro Assay System*, Molecular Dynamics (1996).

Product Literature: *Victor's Technical Side, Continous Light Source For Flurometric And Photometgric Measurements*, Wallac Oy, Finland & EG&G Berthold.

Product Literature: *Spectra Max 250 Microplate Spectrophotometer*, Molecular Devices (1994).

TUNABLE EXCITATION AND/OR TUNABLE DETECTION MICROPLATE READER

This is a Continuation-In-Part of U.S. patent application Ser. No. 08/405,468, filed Mar. 16, 1995, now U.S. Pat. No. 5,591,981, the entire disclosure of which is incorporated herein by reference.

BACKGROUND OF THE INVENTION

The present invention relates generally to microplate readers and, more particularly, to a method and apparatus for measuring the luminescence, fluorescence, and absorption of a sample in which the excitation and/or detection wavelengths are tunable.

In the biotechnical field, the fluorescence and luminescence properties of samples are routinely measured.

Furthermore, it is often desirable to use a fluorescent probe or dye to mark a particular biological structure such as a malignant tumor or a specific chromosome in a DNA sequence, and then use the fluorescent probe or dye as a means of locating the structure. A variety of devices have been designed to read fluorescent-labeled samples.

In general, a device designed to read and/or image a fluorescent-labeled sample requires at least one light source emitting at one or more excitation wavelengths and means for detecting one or more fluorescent wavelengths. Typically a device designed to read and/or image a luminescent sample requires means for detecting one or more wavelengths as well as means for adding one or more reagent lines. Reagents are typically added to the sample in order to initiate the luminescence phenomena. A device designed to measure sample absorption requires means for determining the amount of light transmitted through the sample in question. Furthermore, it is often desirable to determine the wavelength dependence of the transmittance.

In U.S. Pat. No. 5,290,419, a multi-color fluorescence analyzer is described which irradiates a sample with two or more excitation sources operating on a time-shared basis. Band pass filters, image splitting prisms, band cutoff filters, wavelength dispersion prisms and dichroic mirrors are use to selectively detect specific emission wavelengths.

In U.S. Pat. No. 5,213,673, a multi-colored electrophoresis pattern reading apparatus is described which irradiates a sample with one or more light sources. The light sources can either be used individually or combined into a single source. Optical filters are used to separate the fluorescence resulting from the irradiation of the sample into a plurality of fluorescence wavelengths.

In U.S. Pat. No. 5,190,632, a multi-colored electrophoresis pattern reading apparatus is described in which one or more light sources are used to generate a mixture of light capable of exciting two or more fluorescent substances. Both optical filters and diffraction gratings are used to separate the fluorescence by wavelength.

In U.S. Pat. No. 5,062,942, a fluorescence detection apparatus is described in which a fluorescent light image is separated into a plurality of virtual images. Bandpass filters are used to separate the virtual images by wavelength.

In an article by Cothren et al. entitled "Gastrointestinal Tissue Diagnosis by Laser-Induced Fluorescence Spectroscopy at Endoscopy," *Gastrointestinal Endoscopy* 36 (2) (1990) 105-111, the authors describe an endoscopic system which is used to study autofluorescence from living tissue. The excitation source is monochromatic with a wavelength of 370 nanometers. Optical fibers are used to collect the fluorescence emitted by the irradiated tissue. Emission spectra are collected from 350 to 700 nanometers using an imaging spectrograph coupled to a gated optical multi-channel analyzer. A similar autofluorescence system was described by Andersson et al. in "Autofluorescence of Various Rodent Tissues and Human Skin Tumour Samples," *Lasers in Medical Science* 2 (41) (1987) 41-49.

Fluorescence analyzers in general suffer from a number of performance disadvantages. For example, typically such systems have a very limited selection of available excitation wavelengths; detection is generally limited to discrete wavelength bands; the systems normally do not have the ability to measure luminescence and/or absorption; samples must be contained in one of only a few configurations; and if microplates are used, it is not possible to obtain multiple readings within a single sample well.

From the foregoing, it is apparent that a microplate reader is desired which can measure the wavelength dependence of the fluorescence, luminescence, and absorption properties of a sample at multiple locations within a single sample well of a microplate.

SUMMARY OF THE INVENTION

The present invention provides a microplate reader capable of making readings within multiple locations within each sample well of the microplate. The apparatus measures fluorescence, luminescence, and absorption at each selected location. The excitation and/or detection wavelength is tunable, thus allowing the wavelength dependence of the various properties to be determined.

The tuning section of the excitation and/or detection subassemblies can utilize dispersive elements, diffractive elements, filters, or interferometers. Examples of dispersive and diffractive elements are prisms and gratings, respectively. Examples of filters are short pass filters, long pass filters, notch filters, variable filters, acousto-optic filters, polarization filters, interference filters based on continuously varying film thickness, and tunable liquid crystal filters. Examples of interferometers include Fabrey-Perot etalons and common path interferometers.

In one embodiment of the invention, the user inputs the type of sample container, i.e., a microplate with 6, 12, 24, 48, 96, or 384 wells. The user can also select to analyze a gel or a storage phosphor plate. Once the type of sample and sample container are selected, the user enters the number of locations per sample well which are to be analyzed. The user can either select to use a predetermined test pattern or specify the actual testing locations. The user can also select to run a pseudo-continuous test pattern in which the microplate is moved in a serpentine pattern during analysis, thus mapping out the entire microplate.

A further understanding of the nature and advantages of the present invention may be realized by reference to the remaining portions of the specification and the drawings.

DESCRIPTION OF THE PREFERRED EMBODIMENT

Figure 1:
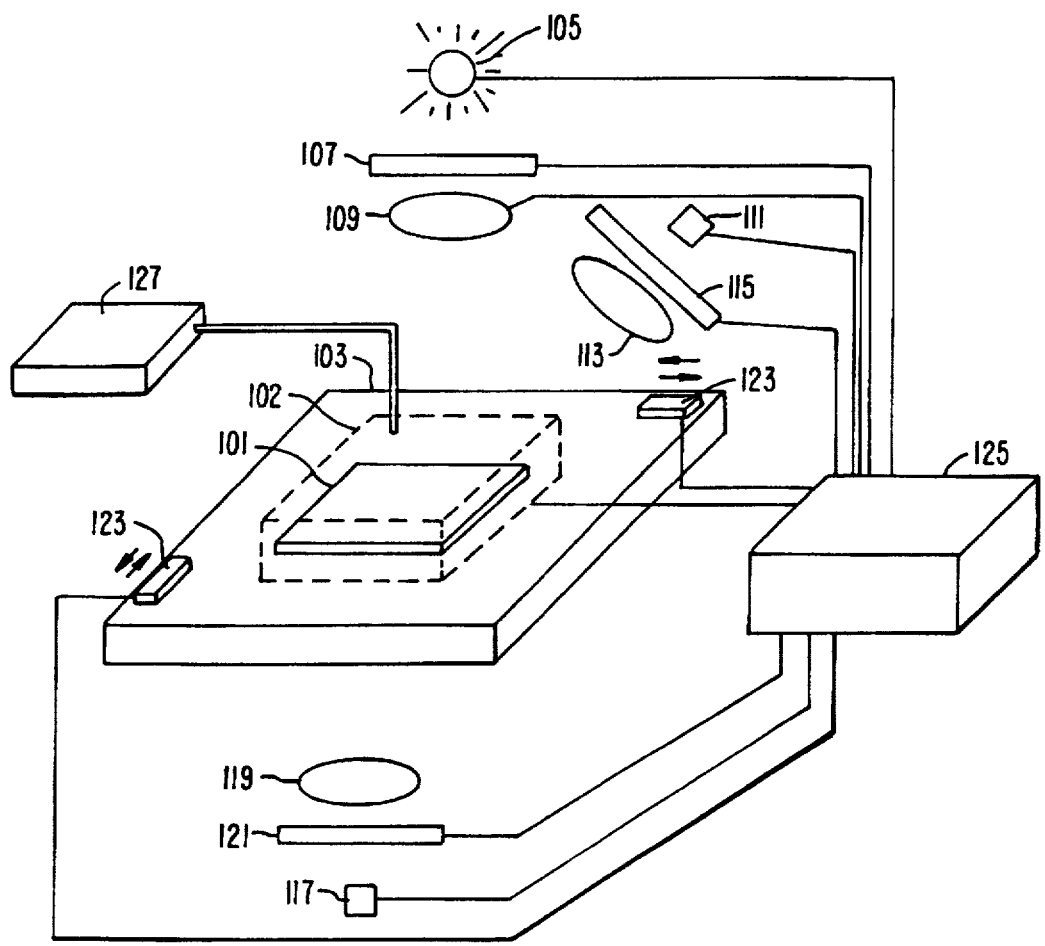
FIG. 1 is an illustration of one embodiment of the invention.

FIG. 1 is an illustration of an embodiment of the invention. A sample 101 can be any of a variety of materials which have been treated with a fluorochrome dye or probe. Sample 101 can also be a sample which exhibits autofluorescence or luminescence. Sample 101 can also be a sample on which only a subset of the possible tests are to be performed, for example absorption. Sample 101 is housed in a temperature controlled incubator 102.

Sample 101 is held in place for testing by a holding fixture 103. A wide variety of samples can be held in fixture 103 with few, if any, fixturing adjustments. For example, 6, 12, 24, 48, 96, and 384 well microplates can be interchangeably used with this fixture. Gel plates and storage phosphor plates can also be used with this fixture.

A light source 105 illuminates sample 101. If desired for a specific test, for example luminescence measurements, light source 105 can be deactivated. Although preferably the wavelength range of light source 105 is from approximately 250 nanometers (i.e., ultraviolet radiation) to 2 micrometers (i.e., infrared radiation), a smaller subset of this range is adequate for most present applications. Light source 105 can be a single source, for example a xenon arc lamp with a relatively flat output from approximately 320 to 700 nanometers. By changing the fill gas (e.g., argon instead of xenon), the temperature of the fill gas, and the material comprising the lamp envelope, different wavelength bands are obtainable. Light source 105 can also be a laser operating at one or more wavelengths. To obtain a broader wavelength band, the output of two or more sources can be combined. Beam splitters or optical fibers can be used to combine the outputs of the individual sources. It is possible to combine the outputs of the individual sources such that all sources emit simultaneously and, in the case of multiple laser sources, co-linearly. However, in the preferred embodiment either the user or the system in automatic mode determines the appropriate wavelength or wavelength band for the selected application and activates the appropriate source.

The radiation emitted by source 105 passes through a tuning section 107 and focussing optics 109 prior to irradiating sample 101. Fluorescence and/or luminescence is imaged onto a detector 111 after passing through imaging optics 113 and a tuning section 115. Detector 111 and associated optics 113 and tuning section 115 can be mounted in a variety of locations in order to optimize performance, including both above and below sample 101.

A second detector 117 is mounted below sample 101 and is used for absorption measurements. Detector 117 can be operated either independently of or simultaneously with detector 111. Light from source 105 passing through sample 101 is imaged onto detector 117 by imaging optics 119. Prior to being imaged, the transmitted radiation passes through a neutral density (hereafter, ND) filter 121. The value for the ND filter 121 is selected by the user (or by the system when operated in automatic mode), thus allowing detector 117 to measure a broad range of transmittances while operating in its optimal sensitivity range.

Fixture 105 is coupled to a pair of positioners 123. Positioners 123 allow sample 101 to be moved in two orthogonal directions (i.e., X and Y) with respect to source 105, detector 111, and detector 117. Although in this embodiment sample 101 is moved, it is also possible to move the source and the detector(s) and keep the sample stationary. In this alternate embodiment, fiber optics can be used to provide a flexible optical light delivery and detection system.

Although the system can be controlled manually, preferably a data processor 125 is used to control the various aspects of the system as well as store the output data from the detectors. In the preferred embodiment, processor 125 is coupled to tuning sections 107 and 115, ND filter system 121, light source 105, focussing optics 109, detectors 111 and 117, and positioners 123. Processor 125 also controls the temperature of incubator 102. Although processor 125 can be used to store the raw data from the detectors, preferably processor 125 places the data in a user defined format.

Preferably processor 125 also controls the system gain settings, the sampling time, and the delay, if any, between the source flash and the sampling period.

The present invention can be used for investigating both fluorescence and luminescence phenomena. Typically for fluorescence measurements, a probe is attached to the area of interest, for example a specific chromosome region. Currently the number of useful dyes is relatively limited. In order to increase the number of probes that may be imaged in a given experiment, combinatorial fluorescence approaches have been developed. In a combinatorial approach fluorescent reporter groups are used either singularly or in combination. The table below illustrates how three fluorescent reporters, A, B, and C can be used for up to seven probes. The number of detectable probes can be increased to fifteen with four fluorophores and to twenty six with five dyes.

| Probe Number | Reporter Combination |
| --- | --- |
| 1 | A |
| 2 | B |
| 3 | C |
| 4 | A + B |
| 5 | B + C |
| 6 | A + C |
| 7 | A + B + C |

Figure 2:
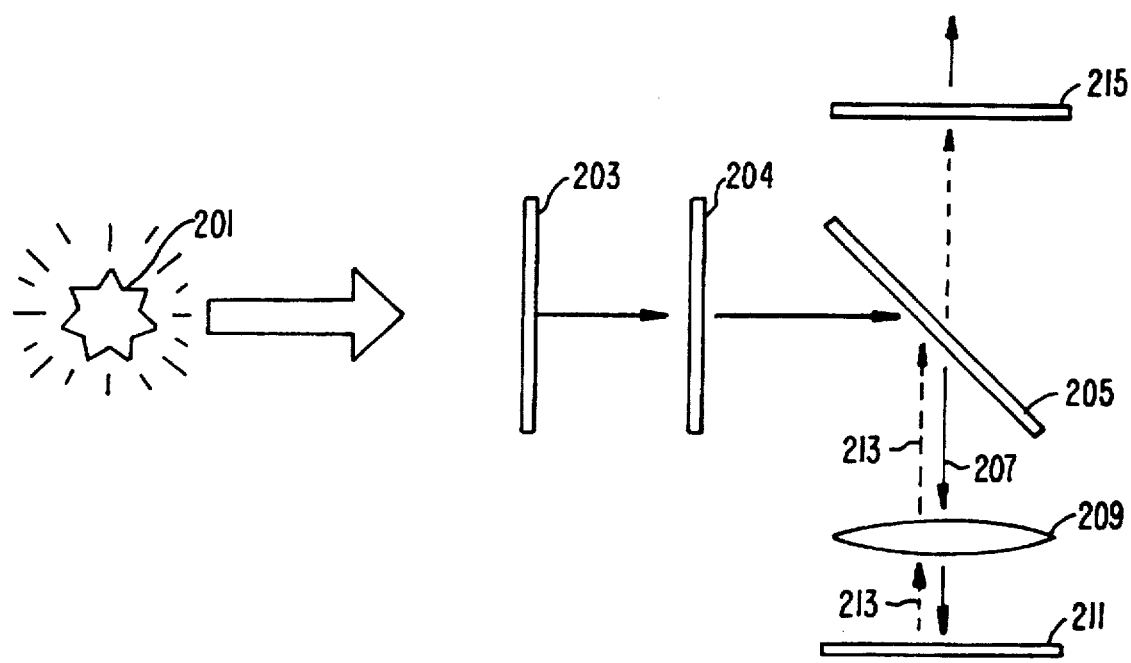
FIG. 2 is an illustration of one aspect of the optical train in one embodiment of the invention.

Although a number of techniques for illuminating sample 101 can be used with the present invention, FIG. 2 illustrates a specific configuration which is well suited for investigating fluorescence phenomena. Light emitted from a source 201 first passes through optional broadband filter 203.

Filter 203 is used to remove large bands of undesirable radiation. For example, filter 203 can be used to remove IR radiation. The light then passes through a tuning assembly 204 which passes the wavelength band of interest. Depending upon the application, assembly 204 can be as simple as an optical filter, or as complex as a continuous wavelength tuning system. In this embodiment, after the light passes through assembly 204, the light impinges on a beamsplitter 205 which reflects the desired wavelengths. For example, beamsplitter 205 may only reflect those wavelengths necessary to excite a selected fluorochrome. The reflected radiation then passes along light path 207, through condensing optics 209, and impinges on sample 211. The incident light causes the fluorochromes on the various probes to fluoresce, the emitted fluorescence following path 213. Also following path 213 is light which was scattered by sample 211. In order to accurately measure the emitted fluorescence, the scattered radiation is removed. The light leaving sample 211 and following path 213 is incident on beamsplitter 205. Since the reflection coating on beamsplitter 205 is designed to reflect those wavelengths necessary for exciting the selected fluorochromes while passing all other radiation, beamsplitter 205 removes the scattered light by reflecting it away from path 213 while passing the emitted fluorescence. The emitted fluorescence is further filtered using filter 215. At this point the light is ready for spectral dissection and detection.

In the preferred embodiment of the invention, both the wavelength and the bandwidth of the excitation radiation as well as the wavelength and the bandwidth monitored by the detectors are tunable. Although specific applications may require only the ability to control the wavelength of either the excitation or the detection subsystems, by providing control of both it is easy to obtain a detailed spectral analysis of a sample. In an alternate embodiment of the invention, complete tunability is only provided in one subsystem (i.e., excitation or detection subsystem), while course tuning (e.g., using a set of filters) is provided in the other subsystem.

A number of techniques can be used for spectral discrimination with either the excitation or detection subsystems. These techniques fall into four categories: dispersive elements, diffractive elements, interferometric elements, and filters.

Figure 3:
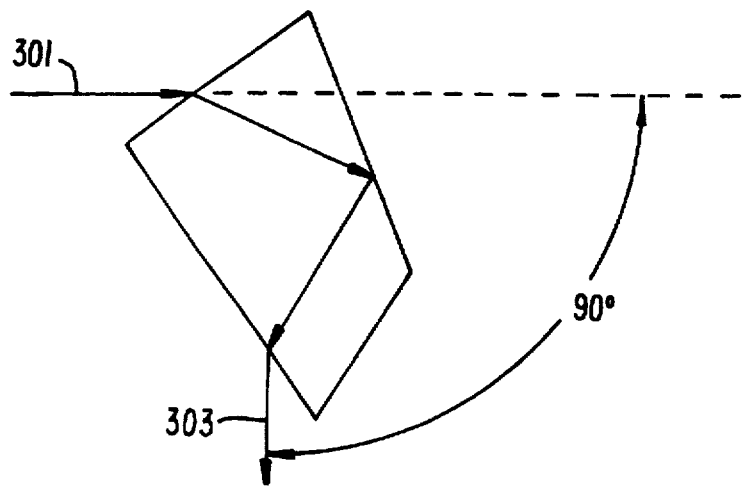
FIG. 3 is an illustration of a Pellin-Broca prism.

A prism is a dispersive element which, in its standard form, is non-linear as a function of deviation. This non-linearity results in a rather complex optical apparatus design. Therefore to minimize the complexity of the optical design, it is preferable to use a constant deviation dispersing prism such as the Pellin-Broca prism shown in FIG. 3. In this type of prism a single monochromatic ray 301 will pass through the prism and exit at a deviation of 90 degrees from the initial incident beam 303. All other wavelengths will emerge from the prism at different angles. By rotating the prism along an axis normal to the plane of the image in FIG. 3, the incoming ray will have a different angle of incidence and a different wavelength component will exit the prism at a deviation of 90 degrees. This type of prism obviously simplifies the design of the apparatus since the system can operate at a fixed angle and the wavelength can be tuned by rotating the prism.

Figure 4:
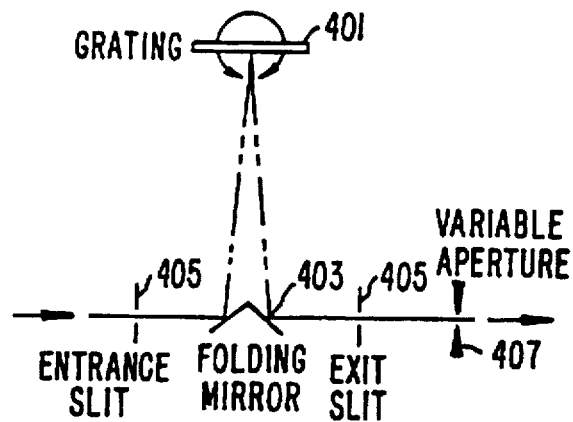
FIG. 4 is an illustration of a wavelength dispersive system using a grating.

A grating can also be used to spectrally disperse the emitted fluorescent spectra. FIG. 4 shows one configuration of a wavelength diffractive system comprising grating 401, folding mirror 403, entrance and exit slits 405, and aperture 407. The wavelength is tuned by rotating grating 401. The bandwidth of this system is a function of the grating groove spacing, the aperture diameter, and the distance between the aperture and the grating. In the preferred configuration of this embodiment multiple gratings are used which can be remotely selected depending upon the wavelength region of interest. Using multiple gratings insures that sufficient radiation is collected within all of the spectral bands of interest.

Figure 5:
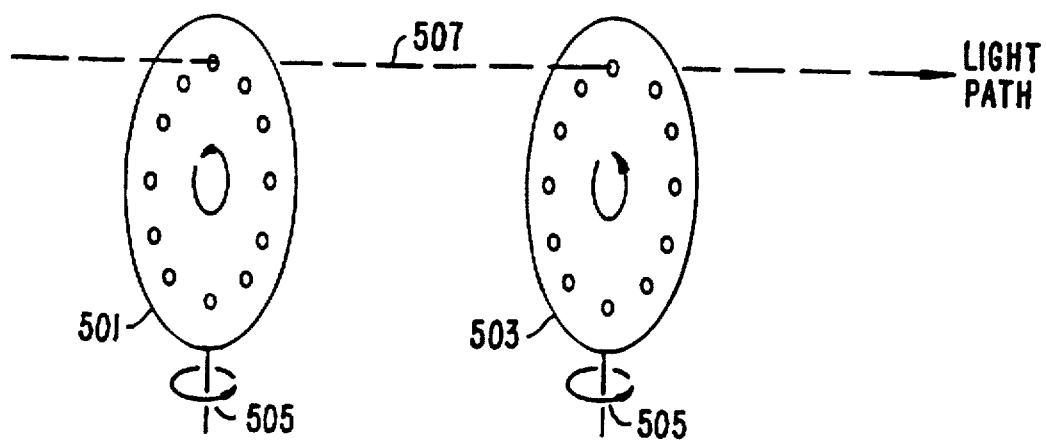
FIG. 5 is an illustration of a dual filter wheel approach to obtaining wavelength tunability.

Another approach to tuning the wavelength in either the excitation or detection sections of the invention is through the use of optical filters. In FIG. 5 a filter wheel 501 contains a series of filters with a short pass edge while a filter wheel 503 contains a series of filters with a long pass edge. Therefore both the wavelength as well as the bandwidth is determined by the choice of filters. For example, by selecting a short pass filter of 450 nanometers and a long pass filter of 470 nanometers a 20 nanometer band centered at 460 nanometers is selected. In order to insure that the wavelength is continuously tunable, filter wheels 501 and 503 not only rotate to allow the selection of a particular filter, but they also can be rotated about axes 505. This results in the filters being tilted with respect to optical axis 507. As the filters are tilted off-axis their wavelength characteristics gradually change.

Another approach to tuning the wavelength is to use variable filters. Circular variable filters are simply interference filters in which the film thickness varies linearly with the angular position on the substrate. An embodiment using circular variable filters would be similar in appearance to the configuration shown in FIG. 5 except that filter wheels 501 and 503 are replaced with the circular variable filters. Depending upon the position of each filter wheel and the tilt along axes 505, any wavelength can be chosen. By controlling the amount of light illuminating the filters, through the use of slits, the bandwidth can also be controlled.

In another embodiment, a Fabrey-Perot etalon tunable filter can be used to tune the wavelength of the excitation and/or detection sections of the invention. In this embodiment it is generally preferable to eliminate most of the undesired wavelengths using a bandpass filter. Then the fine tuning is performed using the Fabrey-Perot system. In a variation of this system, ferroelectric liquid crystal devices can be inserted into the interference filters of the Fabrey-Perot etalon. This design is capable of high throughput as well as rapid fine tuning of the system.

Figure 6:
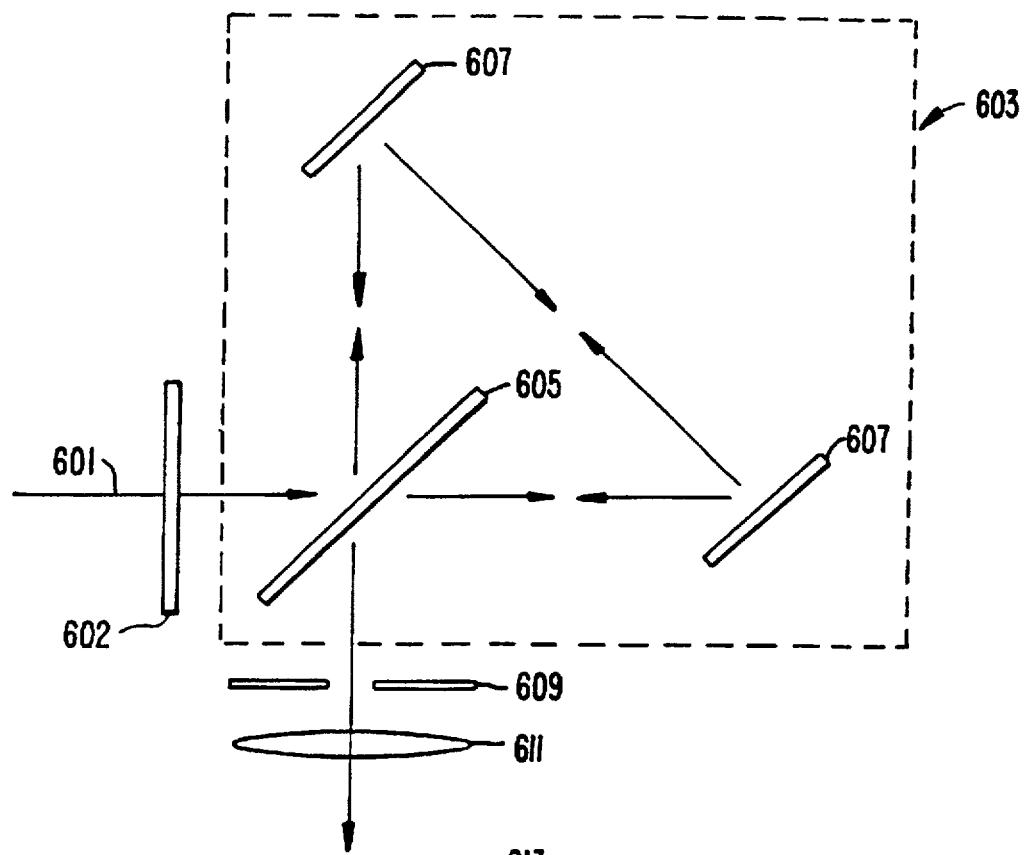
FIG. 6 is an illustration of a SAGNAC interferometer.

The preferred embodiment of the emission detection system is shown in FIG. 6. In this embodiment the radiation 601 emitted by the sample is first filtered to remove much of the undesired wavelength spectra using an optical filter 602.

After filtering, radiation 601 enters a SAGNAC interferometer 603. SAGNAC interferometer 603 is comprised of a beam splitter 605 and turning mirrors 607. Wavelength selection is accomplished by controlling the optical path difference of the interferometer. Adjustable slit 609 controls the bandwidth. Optics 611 focus the radiation passing through the interferometer and produce a real image onto detector 613. In this embodiment detector 613 is a CCD array and there is a one to one correspondence between the sample and the projected image of the sample.

As illustrated in FIG. 6, beamsplitter 605 divides the incoming light into two separate beams. These beams are recombined to form an interference pattern at detector array 613. The pattern's intensity at each pixel of array 613 varies with the optical path difference. By measuring the intensity versus the optical path difference, an interferogram is created. In order to recover the wavelength spectra at each pixel of array 613, a Fourier transform of each interferogram is calculated, preferably using processor 125.

Figure 7:
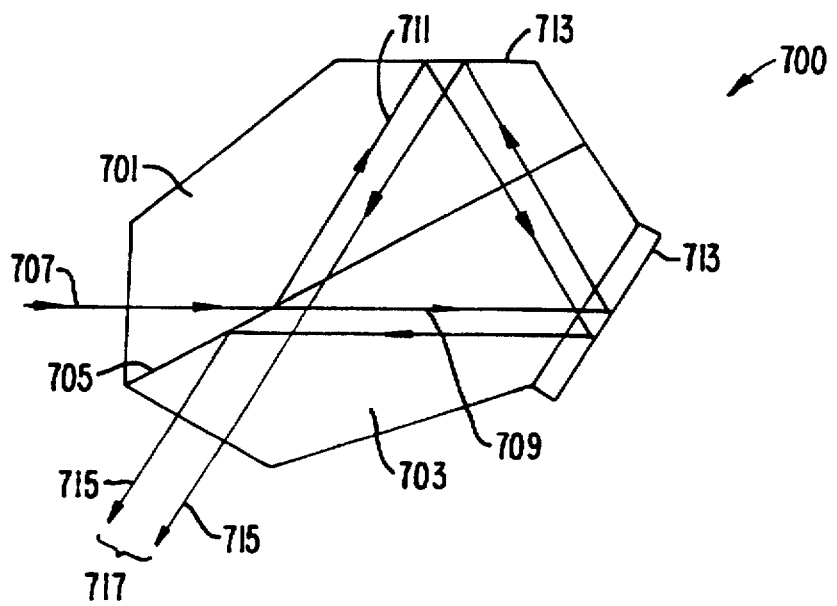
FIG. 7 is an illustration of a monolithic interferometer.

FIG. 7 illustrates a monolithic form of an interferometer 700. The monolithic interferometer is more immune to vibration, misalignment, and thermal effects then other interferometer configurations. This form of interferometer has a very large acceptance angle.

Interferometer 700 is comprised of a first piece of glass 701 bonded to a second piece of glass 703 along the plane of a beamsplitter coating 705. Light is incident on the interferometer along path 707. When this light ray hits beamsplitter coating 705, the ray is split into two rays, one ray following path 709 and the other ray following path 711. After being reflected by interferometer mirrors 713, the rays exit the optic along paths 715 separated by a distance 717.

In at least one embodiment of the invention, light source 105 can be temporarily disabled so that luminescence measurements can be performed. Source 105 can either be disabled manually through user selection, or automatically by processor 125 when a luminescence test is selected. After disablement of source 105, reagents from one or more reagent lines can be dispensed into sample 101 from reagent dispensing mechanism 127. Preferably the reagents are dispensed within distinct wells of a multi-well microplate. The time between dispensing the reagents and taking a reading is adjustable.

In at least one embodiment of the invention, absorption measurements are made using detector 117. In this embodiment a specific wavelength band for the excitation radiation is selected using tuning section 107. By measuring the amount of light transmitted through sample 101, the absorption characteristics of sample 101 can be determined. In order to achieve a wide range of measurement sensitivity a series of ND filters 121 are interposed between sample 101 and detector 117. Preferably ND filters 121 are contained in a filter wheel. In one configuration, processor 125 determines the appropriate ND filter based on the output of detector 117. In an alternate configuration, a secondary detector (not shown) is placed in close proximity to detector 117. The secondary detector is less sensitive to overexposure and therefore can be used to select an appropriate ND filter 121, thus minimizing the risk of damaging detector 117.

Figure 8:
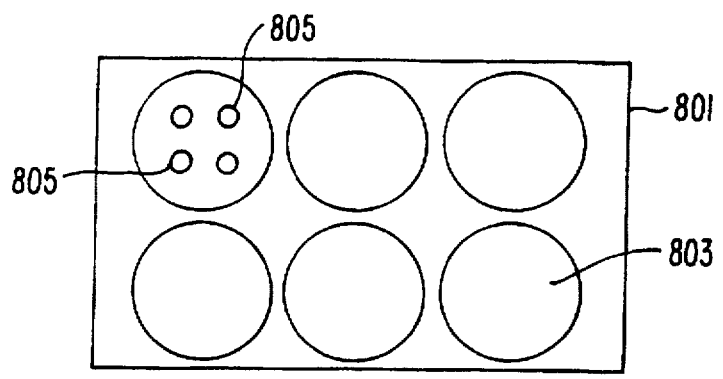
FIG. 8 is an illustration of the cross-section of a multi-well microplate containing 6 wells.

Samples 101 contained in a variety of sample containers can be analyzed with the present invention. FIG. 8 is an illustration of the cross-section of a typical microplate 801 containing 6 sample wells 803. In a microplate of this type, each well 803 contains an individual specimen. After sample preparation, microplate 801 is placed within holding fixture 103. The preferred embodiment of the present invention is capable of utilizing microplates with 6, 12, 24, 48, 96, or 384 wells. The preferred embodiment can also analyze gels and storage phosphor plates. Preferably, the user enters the desired sample configuration into processor 125. Processor 125 then determines the appropriate sample reading strategy based on the user selected configuration.

The present invention is capable of analyzing sample 101 at multiple locations within each individual sample well. In other words, if a 6 well microplate is selected, such as the microplate illustrated in FIG. 8, the user is able to obtain fluorescence, luminescence, and absorption information (depending upon the configuration of the invention) at multiple locations within each sample well 803.

In one embodiment of the invention, the user specifies the sample configuration (e.g., a microplate with 6 wells) and the number of locations within each well to be tested. In this embodiment, data processor 125 determines the locations of the testing based on a predetermined test pattern. For example, if the user selects four sample locations and a 6 well microplate, processor 125 would then test each sample well at four locations 805.

Figure 9:
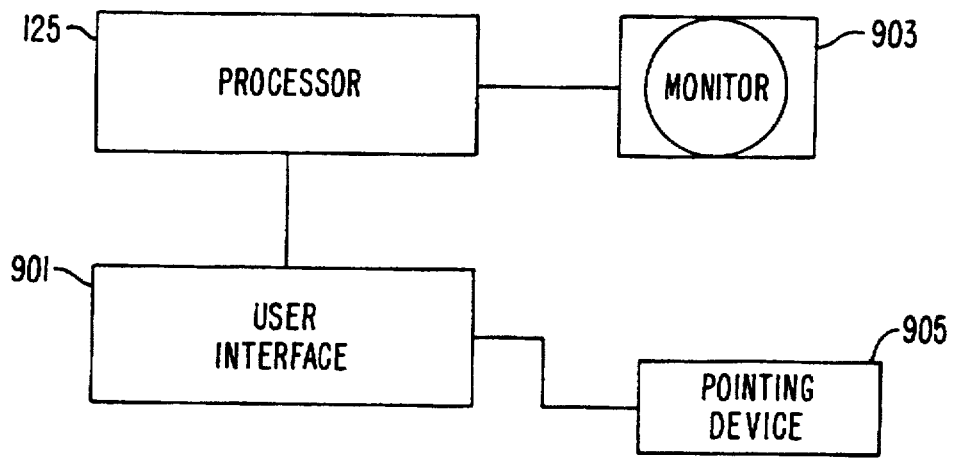
FIG. 9 is a functional block diagram of an alternate embodiment in which the user can specify the actual locations within a sample well at which testing is to be performed.

FIG. 9 is a functional block diagram of an alternate embodiment in which the user can specify the actual locations within a sample well at which testing is to be performed. Preferably, processor 125 is coupled to a user interface 901 such as a keyboard. Processor 901 is also coupled to a monitor 903. After the user selects a sample configuration using interface 901, a schematic representation of the selected sample configuration is presented on monitor 903. The user then indicates a specific sample well to be analyzed using interface 901. Alternatively, the user can indicate the sample well of interest using a pointing device 905 (e.g., a mouse). In the preferred embodiment, once a sample well has been selected, monitor 903 presents a magnified view of a single well. The magnified view makes it easier for the user to indicate the areas for measurement. The user indicates the specific areas within the selected sample well which are to be analyzed using either interface 901 or pointing device 905. After the locations have been entered, the system can then be programmed to either analyze only the selected sample well or to use the same locations for measuring every sample well within the microplate. These locations may also be stored for later use with subsequent microplates.

In an alternate configuration, after a sample plate has been analyzed, the resultant data is presented on monitor 903. For example, the user can specify that absorption readings are to be taken at four locations within each sample well of a 6 well microplate. After analysis, processor 125 would present on monitor 903 the optical density readings at each analyzed location for each well. The user can then select to have additional readings made on new testing locations by indicating the new locations using interface 901 or pointing device 905.

In an alternate embodiment of the invention, the processor performs a pseudo-continuous analysis of sample 101. In this embodiment after the user selects the sample configuration, the step size between successive locations as well as the sampling time are selected. If desired, for example to locate areas of interest within each sample well, the system can be placed in a continuous mode. In this mode readings are taken in a continuous fashion as the system scans through the microplate. Preferably the processor is configured to allow the user to select the total number of scanning passes, thus determining how many scanning passes per sample well are performed. If desired, and depending upon the selected illumination beam size, the system can also be configured to scan the microplate with an overlapping pattern. Utilizing this scanning configuration, subsequent passes through a sample well overlap by a predetermined amount the previous passes through the same sample.

Figure 10:
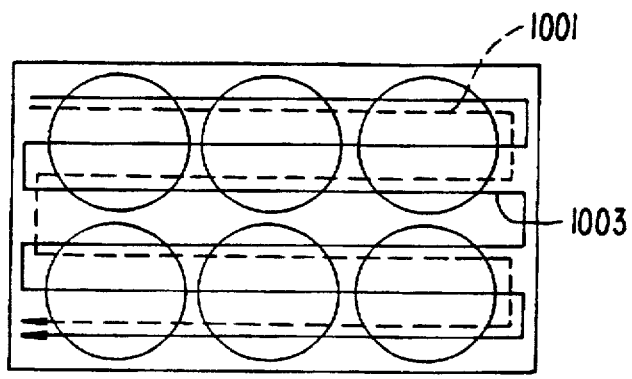
FIG. 10 is an illustration of two scanning patterns for a 6 well microplate.

FIG. 10 is an illustration of two scanning patterns for a 6 well microplate. In pattern 1001 a series of finely spaced readings are made such there are two passes for each sample well. In this example for each pass through each sample well, 10 readings are made. Pattern 1003 is a continuous pattern in which the readings are made in a serpentine fashion. Pattern 1003 allows three passes per sample well.

The depth of focus of the illumination beam is controlled by optics 109. The depth of focus of the beam can be used as a means of controlling the signal-to-noise (i.e., S/N) ratio of the system. For example in some samples such as gels, the concentration of the fluorescing material may vary vertically within the sample. Therefore by controlling the depth of focus it is possible to optimize the location and size of the collection volume, thus maximizing the S/N ratio.

The diameter of the illumination beam is controlled by optics 109. In one embodiment of the invention, the beam diameter is large compared to the diameter of a single sample well. Thus a large portion of the sample well is irradiated. In this embodiment the detector monitoring the sample (i.e., either detector 111 or 117) is also large in comparison to the sample well diameter. As a result of this configuration, the measurement of a single sample well yields an average value for the cell, either in terms of average fluorescence or average absorption.

In an alternate embodiment of the invention, although the illumination beam diameter is large, the detector diameter is small. In this embodiment the position of the detector is independent of that of the illumination beam. Thus a user is able to position the detector to take readings of a specific point within a sample cell without moving the illumination beam.

In an alternate embodiment of the invention, the illumination beam diameter is large compared to the diameter of the sample well and the detector is comprised of a plurality of individual pixels. In this configuration the user is able to simultaneously obtain readings for locations throughout the sample well, the measurement locations being defined by the pixel locations.

In an alternate embodiment of the invention, the illumination beam diameter is small compared to the diameter of the sample well. The diameter of the detector in this embodiment is either on the same order as that of the illumination beam, or larger than the illumination beam. In this configuration the position of the illumination beam determines the area within the sample well which is to be interrogated.

In the preferred embodiment of the invention optics 109 is controlled by processor 125. This embodiment allows a user, through user interface 901, to vary the beam diameter and/or the depth of focus depending upon the desired application and/or the detector configuration. If the apparatus is operated in the automatic mode, processor 125 can be used to vary the diameter of the beam and/or the depth of focus depending upon the testing configuration entered by the user. Therefore if the user entered testing configuration is a 384 sample well microplate, processor 125 causes the beam diameter to be smaller than if the microplate configuration is a 6 sample well microplate. In an alternate automatic mode, the beam diameter may remain constant regardless of the microplate configuration due to limitations imposed by the detector size. However, processor 125 may still be used to automatically vary the beam diameter depending upon the selected test. For example, the detector used for absorption measurements may be of a larger diameter than the detector used for fluorescence measurements. Thus processor 125 would vary the beam diameter accordingly.

The present invention can be used to determine the fluorescence, luminescence, or absorption at a specific wavelength or band of wavelengths for a specific location on a sample, this information being provided to the user in the form of a detector output signal. However, in the preferred embodiment of the invention, an image of the sample is formed and presented to the user on a monitor. It is not required that the apparatus have the capability to form an image of both the fluorescence and luminescence information as well as the absorption information. Rather, it may be desirable to form an image based on only one of these measurements while providing the user with a simple 'value' for the other measurements.

Figure 11:
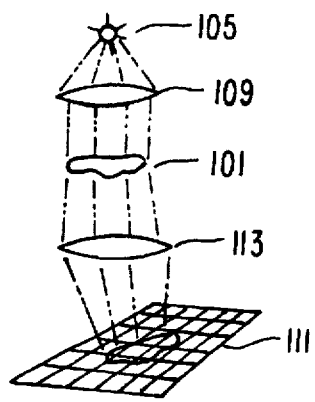
FIG. 11 shows a functional block diagram of one embodiment of the detection system.

In the preferred embodiment detector 111 is a charge coupled device (CCD) array. FIG. 11 is an illustration of one aspect of the invention in which sample 101 is irradiated by source 105, the source radiation first being focussed by optics 109. The emissions from sample 101 are collected and focussed by optics 113 onto detector array 111. FIG. 11 does not illustrate any of the system's wavelength tuning capabilities nor does it illustrate either the luminescence or absorption measurement capabilities. One skilled in the art will recognize that a similar technique could be used to image either of these other quantities. In this embodiment there is a one-to-one correspondence between sample 101 and the image detected by detector 111. Thus a first portion of sample 1 is imaged onto a first pixel; a second portion of sample 1 is imaged onto a second pixel, etc.

Once the spectral data for each pixel of array 111 has been determined, processor 125 can be used to generate a variety of useful images on monitor 903. For example, if probes are being used to map chromosome regions, the probes can be viewed either individually or in a variety of combinations, including showing all identified probes simultaneously. Thus, if at least five different dyes are used, it is possible to create a karyotype with each chromosome individually identified. Since many of the probes will contain multiple dyes (i.e., combinations of dyes in a single probe), pseudo-coloring can be used to simplify the presented image. In this scheme each probe is assigned an easily distinguishable color. For example, if three dyes were used to form seven probes, four of the probes would be formed by some combination of dyes. By assigning each probe, including those with multiple dyes, an individual color, the image presented to the user is quite simple and straightforward. The processor can also be used to enhance the image as well as provide intensity profiles (e.g., different colors assigned to different measured intensities).

Figure 12:
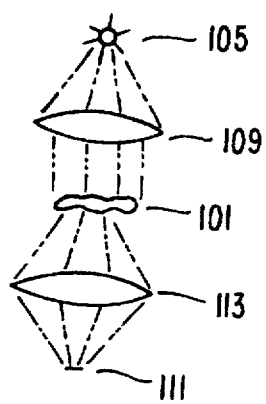
FIG. 12 shows an alternate embodiment of the detection system.

FIG. 12 shows an alternate embodiment of the detection system. In this embodiment optics 113 focus the emission from a first portion of sample 101 onto a single detector 111. Detector 111 may be a CCD, a cooled CCD, a photomultiplier tube, a silicon photodiode, or any other detector which is sensitive to the wavelengths of interest. By raster scanning either focussing optics 113 or sample 101, different portions of sample 101 are serially focussed onto detector 111. Processor 125 then reconstructs an image of sample 101 which can be displayed on monitor 903.

Figure 13:
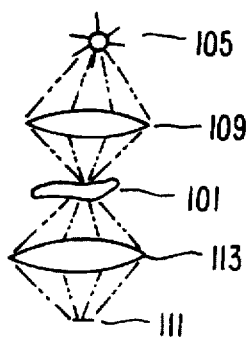
FIG. 13 shows a third embodiment of the detection system.

FIG. 13 shows a third embodiment of the detection system. In this embodiment radiation from source 105 is focussed by optics 109 onto a small portion of sample 101. Emitted radiation of this portion of sample 101 is then captured and focussed by optics 113 onto detector 111. Sample 101 is raster scanned, thus allowing an entire image to be serially captured and recorded. This embodiment is especially beneficial when weak probes are used, since both the excitation radiation and the emitted fluorescence are focussed.

In at least one embodiment of he invention, processor 125 includes a look-up table. The look-up table performs a series of functions. First, the look-up table can instruct the user as to the optimum system operating parameters (i.e., excitation and emission wavelengths, excitation and emission bandwidths, illumination beam diameter, sampling time, sample scanning configuration, ND filter requirements, etc.) for a specific experimental configuration. Second, the look-up table in combination with processor 125 can be used to compensate for variations in the system. For example, the user may want to distinguish between the quantities of two different fluorescing substances within the sample. The user would most likely be in error to rely simply on the relative intensities of these two different substances. This is because each element of the optical train, from the source to the detector, is likely to exhibit some degree of wavelength dependence. All of this variational information can be programmed into the look-up table. Then, if desired, the system can automatically correct the final image for these variations.

Processor 125 can be used in conjunction with a peaking algorithm to optimize the system's output. Peaking allows the user to compensate for the environmental sensitivity of a label, this sensitivity resulting in fluorescence spectral shifts. In practice, the user can either chose the initial settings for the excitation and emission detection wavelengths as well as the bandwidths of each, or the user can allow the system to automatically chose these settings on the basis of the selected dye or probe (relying on information contained in a look-up table). If the user next selects through interface 901 that the signal be peaked, the system will automatically peak the signal using the peaking algorithm. In the preferred embodiment algorithm is a simple set of feedback loops. The signal from the detector is monitored while the source wavelength, the emission detection wavelength, and the bandwidth of both the source and detection system are varied around the initial settings. This peaking process can either be performed for a set number of times or the difference between the signal-to-noise measured at the previous setting and that measured for the currently "peaked" setting can be monitored with the process being automatically stopped when the difference becomes less than some predefined value.

As will be understood by those familiar with the art, the present invention may be embodied in other specific forms without departing from the spirit or essential characteristics thereof. Accordingly, disclosure of the preferred embodiment of the invention is intended to be illustrative, but not limiting, of the scope of the invention which is set forth in the following claims.

We claim:

1. A multilabel counting apparatus, comprising:
   a sample holding stage;
   a source for illuminating a sample within said sample holding stage with radiation within a first band of wavelengths, wherein said first band of wavelengths is a subset of the emittance of said source, said first band of wavelengths selected by a first wavelength band selection system, wherein said sample comprises a plurality of individual sample wells;
   at least one projection optic for focussing said radiation from said source onto a selected location of a selected individual sample well wherein said focussed radiation irradiates only a discrete portion of said selected individual sample well;
   a detector for detecting emissions from said discrete portion of said selected individual sample well, wherein a second wavelength band selection system determines the wavelength band of emissions detected by said detector, and wherein said detector generates a plurality of output signals dependent upon the intensity of said emissions within said selected sample emission wavelength band; and
   a moving mechanism for moving the relative positions of said sample holding stage, said source, and said detector, wherein said moving mechanism determines which of said plurality of individual sample wells receives focussed radiation from said source and wherein said moving mechanism determines said discrete portion of said selected individual sample well irradiated by said focussed radiation and from which said emissions are detected.

2. The multilabel counting apparatus of claim 1, wherein said sample is a multiple well microplate.

3. The multilabel counting apparatus of claim 1, wherein the number of said plurality of individual sample wells is selected from the group consisting of 6, 12, 24, 48, 96, and 384 wells.

4. The multilabel counting apparatus of claim 1, wherein said emissions are detected at a plurality of discrete locations within each of a predetermined quantity of said plurality of individual sample wells.

5. The multilabel counting appartus of claim 4, wherein said predetermined quantity of said plurality of individual sample wells is the total quantity of said plurality of individual sample wells.

6. The multilabel counting apparatus of claim 1, wherein said moving mechanism is operable in a continuous manner whereby the relative positions of said sample holding stage, said source, and said detector continuously change, and wherein said emissions are continuously detected by said detector.

7. The multilabel counting apparatus of claim 6, wherein said output signals of said detector are used by a microprocessor to form a bit map image of said sample.

8. The multilabel counting apparatus of claim 7, further comprising a display device for displaying said bit map image, wherein said display device is coupled to said microprocessor.

9. The multilabel counting apparatus of claim 1, wherein said focussed source radiation has a variable diameter.

10. The multilabel counting apparatus of claim 1, wherein said focussed source radiation has a variable depth of focus.

11. The multilabel counting apparatus of claim 1, wherein said source is a xenon flash lamp.

12. The multilabel counting apparatus of claim 1, wherein said source is a laser producing at least one wavelength.

13. The multilabel counting apparatus of claim 1, wherein said detector is selected from the group consisting of a photomultiplier tube, a CCD array, a cooled CCD array, and a silicon photodiode.

14. The multilabel counting apparatus of claim 1, wherein said first and second wavelength band selection systems are selected from the group consisting of prisms, diffraction gratings, short pass and long pass filters, variable filters, acousto-optic filters, polarization dependent filters, interference filters based on continuously varying film thickness, Fabrey-Perot etalon tunable filters, tunable liquid crystal filters, common path interferometers, and SAGNAC interferometers.

15. The multilabel counting apparatus of claim 1, further comprising a filtering element interposed between said sample and said detector, said filtering element selected from the group consisting of bandpass filters, notch filters, and polarization dependent filters.

16. The multilabel counting apparatus of claim 1, further comprising a neutral density filter interposed between said sample and said detector.

17. The multilabel counting apparatus of claim 1, wherein the emittance of said source is between 250 and 750 nanometers.

18. The multilabel counting apparatus of claim 1, wherein said source is comprised of a plurality of individual sources.

19. The multilabel counting apparatus of claim 1, further comprising a look-up table of operating parameters based on a set of user defined testing parameters, wherein said operating parameters include said first band of wavelengths for said illumination radiation and said emission detection wavelength band.

20. The multilabel counting apparatus of claim 1, further comprising a reagent dispensing mechanism for dispensing at least one reagent of a predetermined type and quantity into predetermined sample wells of said plurality of individual sample wells, wherein said source is disabled prior to dispensing said reagent, and wherein said detector is programmable to allow emission detection at a predetermined time interval after activation of said reagent dispensing mechanism.

21. The multilabel counting apparatus of claim 1, wherein said first band of wavelengths has an adjustable bandwidth and said wavelength band of emissions detected by said detector has an adjustable bandwidth.

22. The multilabel counting apparatus of claim 1, wherein said discrete portion of said selected individual sample well is a substantial portion of said selected individual sample well, and wherein said detector has a plurality of pixels for detecting emissions from said discrete portion.

23. The multilabel counting apparatus of claim 22, wherein each of said plurality of pixels outputs an individual output signal dependent upon the intensity of said emissions of a corresponding fragment of said discrete portion.

24. The multilabel counting apparatus of claim 1, wherein said discrete portion of said selected individual sample well is a substantial portion of said selected individual sample well, and wherein said detector output signal is an average of said irradiated discrete portion.

25. The multilabel counting apparatus of claim 1, further comprising an incubator for maintaining said sample at a predetermined temperature.

26. The multilabel counting apparatus of claim 1, further comprising a data processor for monitoring said detector output signals, wherein said data processor optimizes said detector output signals by varying said first band of wavelengths and varying said wavelength band of emissions detected by said detector.

27. An absorption monitoring apparatus, comprising:
- a sample holding stage;
- a source for illuminating a sample within said sample holding stage with radiation within a first band of wavelengths, wherein said first band of wavelengths is a subset of the emittance of said source, said first band of wavelengths selected by a first wavelength band selection system wherein said sample comprises a plurality of individual sample wells;
- at least one projection optic for focussing said radiation from said source onto a selected location of a selected individual sample well wherein said focussed radiation illuminates only a discrete portion of said selected individual sample well;
- a detector for detecting said illumination radiation passing through said discrete portion of said selected individual sample well, and wherein said detector generates a plurality of output signals dependent upon the intensity of said passed illumination radiation; and
- a moving mechanism for moving the relative positions of said sample holding stage, said source, and said detector, wherein said moving mechanism determines which of said plurality of individual sample wells receives focussed radiation from said source and wherein said moving mechanism determines said discrete portion of said selected individual sample well illuminated by said focussed radiation and from which said passed illumination radiation is detected.

28. The absorption monitoring apparatus of claim 27, wherein said sample is comprised of a microplate.

29. The absorption monitoring apparatus of claims 27, wherein said passed illumination radiation is detected at a plurality of discrete locations within each of a predetermined quantity of said plurality of individual sample wells.

30. The absorption monitoring apparatus of claim 27, wherein said moving mechanism is operable in a continuous manner whereby the relative positions of said sample holding stage, said source, and said detector continuously change, and wherein said passed illumination radiation is continuously detected by said detector.

31. The absorption monitoring apparatus of claim 30, wherein said output signals of said detector are used by a microprocessor to form a bit map image of said sample.

32. The absorption monitoring apparatus of claim 31, further comprising a display device for displaying said bit map image, wherein said display device is coupled to said microprocessor.

33. The absorption monitoring apparatus of claim 27, wherein said focussed source radiation has a variable diameter.

34. The absorption monitoring apparatus of claim 27, wherein said focussed source radiation has a variable depth of focus.

35. The absorption monitoring apparatus of claim 27, wherein said first wavelength band selection system is selected from the group consisting of prisms, diffraction gratings, short pass and long pass filters, variable filters, acousto-optic filters, polarization dependent filters, interference filters based on continuously varying film thickness, Fabrey-Perot etalon tunable filters, tunable liquid crystal filters, common path interferometers, and SAGNAC interferometers.

36. The absorption monitoring apparatus of claim 27, further comprising a filtering element interposed between said sample and said detector, said filtering element selected from the group consisting of bandpass filters, notch filters, and polarization dependent filters.

37. The absorption monitoring apparatus of claim 27, further comprising a look-up table of operating parameters based on a set of user defined testing parameters, wherein said operating parameters include said first band of wavelengths for said illumination radiation.

38. The absorption monitoring apparatus of claim 27, further comprising a reagent dispensing mechanism for dispensing at least one reagent of a predetermined type and quantity into predetermined sample wells of said plurality of individual sample wells.

39. The absorption monitoring apparatus of claim 27, wherein said discrete portion of said selected individual sample well is a substantial portion of said selected individual sample well, and wherein said detector has a plurality of pixels for detecting passed illumination radiation from said discrete portion.

40. The absorption monitoring apparatus of claim 39, wherein each of said plurality of pixels outputs an individual output signal dependent upon the intensity of said passed illumination radiation of said discrete portion.

41. The absorption monitoring apparatus of claim 27, wherein said discrete portion of said selected individual sample well is a substantial portion of said selected individual sample well, and wherein said detector output signal is an average of said illuminated discrete portion.

42. The absorption monitoring apparatus of claim 27, further comprising an incubator for maintaining said sample at a predetermined temperature.

43. The absorption monitoring apparatus of claim 27, further comprising a second wavelength band selection system for determining the wavelength band of passed illumination radiation detected by said detector.

44. The absorption monitoring apparatus of claim 27, further comprising a neutral density filter interposed between said sample and said detector.

45. An absorption monitoring apparatus, comprising:

a sample holding stage;

a source for illuminating a sample within said sample holding stage with radiation, wherein said sample comprises a plurality of individual sample wells;

at least one projection optic for focussing said radiation from said source onto a selected location of a selected individual sample well, wherein said focussed radiation illuminates only a discrete portion;

a detector for detecting said illumination radiation passing through said discrete portion of said selected individual sample well, wherein a wavelength band selection system determines the wavelength band of passed illumination radiation detected by said detector, and wherein said detector generates a plurality of output signals dependent upon the intensity of said passed illumination radiation; and a moving mechanism for moving the relative positions of said sample holding stage, said source, and said detector, wherein said moving mechanism determines which of said plurality of individual sample wells receives focussed radiation from said source, and wherein said moving mechanism determines said discrete portion of said selected individual sample well illuminated by said focussed radiation and from which said passed illumination radiation is detected.

46. The absorption monitoring apparatus of claim 45, further comprising a neutral density filter interposed between said sample and said detector.

47. A multilabel counting apparatus, comprising:

a sample holding stage;

a source for illuminating a sample within said sample holding stage with radiation within a first band of wavelengths, wherein said first band of wavelengths is a subset of the emittance of said source, said first band of wavelengths selected by a first wavelength band selection system, wherein said sample comprises a plurality of individual sample wells;

at least one projection optic for focussing said radiation from said source onto a selected location of a selected individual sample well, wherein said focussed radiation illuminates only a discrete portion of said selected individual sample well;

a first detector for detecting emissions from said discrete portion of said selected individual sample well, wherein a second wavelength band selection system determines the wavelength band of emissions detected by said first detector, and wherein said first detector generates a first plurality of output signals dependent upon the intensity of said emissions;

a second detector for detecting said illumination radiation passing through said discrete portion of said selected individual sample well, and wherein said second detector generates a second plurality of output signals dependent upon the intensity of said passed illumination radiation; and a moving mechanism for moving the relative positions of said sample holding stage, said source, said first detector, and said second detector, wherein said moving mechanism determines which of said plurality of individual sample wells receives focussed radiation from said source, and wherein said moving mechanism determines said discrete portion of said selected individual sample well illuminated by said focussed radiation and from which said passed illumination radiation is detected and from which said emissions are detected.

48. The multilabel counting apparatus of claim 47 wherein said sample is comprised of a microplate.

49. The multilabel counting apparatus of claim 47, wherein said emissions and said passed illumination radiation are detected at a plurality of discrete locations within each of a predetermined quantity of said plurality of individual sample wells.

50. The multilabel counting apparatus of claim 47, wherein said moving mechanism is operable in a continuous manner whereby the relative positions of said sample holding stage, said source, and said detector continuously change, and wherein said emissions and said passed illumination radiation are continuously detected by said detector.

51. The multilabel counting apparatus of claim 47, wherein said focussed source radiation has a variable diameter.

52. The multilabel counting apparatus of claim 47, wherein said focussed source radiation has a variable depth of focus.

53. The multilabel counting apparatus of claim 47, wherein said first and second wavelength band selection systems are selected from the group consisting of prisms, diffraction gratings, short pass and long pass filters, variable filters, acousto-optic filters, polarization dependent filters, interference filters based on continuously varying film thickness, Fabrey-Perot etalon tunable filters, tunable liquid crystal filters, common path interferometers, and SAGNAC interferometers.

54. The multilabel counting apparatus of claim 47, further comprising a filtering element interposed between said sample and said first detector, said filtering element selected from the group consisting of bandpass filters, notch filters, and polarization dependent filters.

55. The multilabel counting apparatus of claim 47, further comprising a filtering element interposed between said sample and said second detector, said filtering element selected from the group consisting of bandpass filters, notch filters, and polarization dependent filters.

56. The multilabel counting apparatus of claim 47, further comprising a look-up table of operating parameters based on a set of user defined testing parameters, wherein said operating parameters include said first band of wavelengths for said illumination radiation and said emission detection wavelength band.

57. The multilabel counting apparatus of claim 47, further comprising a reagent dispensing mechanism for dispensing at least one reagent of a predetermined type and quantity into predetermined sample wells of said plurality of individual sample wells.

58. The multilabel counting apparatus of claim 47, wherein said discrete portion of said selected individual sample well is a substantial portion of said selected individual sample well.

59. The multilabel counting apparatus of claim 47, further comprising an incubator for maintaining said sample at a predetermined temperature.

60. The multilabel counting apparatus of claim 47, further comprising a neutral density filter interposed between said sample and said second detector.

61. A multilabel counting apparatus, comprising:

a sample holding stage;

a source for illuminating a sample within said sample holding stage with radiation within a first band of wavelengths, wherein said first band of wavelengths is a subset of the emittance of said source, said first band of wavelengths selected by a first wavelength band selection system, wherein said sample is selected from the group consisting of gels and storage phosphor plates;

at least one projection optic for focussing said radiation from said source onto a selected location of said sample, wherein said focussed radiation irradiates only a discrete portion of said sample;

a detector for detecting emissions from said discrete portion of said sample, wherein a second wavelength band selection system determines the wavelength band of sample emissions detected by said detector, and wherein said detector generates a plurality of output signals dependent upon the intensity of said emissions within said selected sample emission wavelength band; and a moving mechanism for moving the relative positions of said sample holding stage, said source, and said detector, wherein said moving mechanism determines said selected location of said sample.

* * * * *